US011540930B2

United States Patent
Frid

(10) Patent No.: US 11,540,930 B2
(45) Date of Patent: Jan. 3, 2023

(54) IMPLANTABLE ENDOLUMINAL PROSTHESIS

(71) Applicants: Noureddine Frid, Beersel (BE); CARDIATIS S.A., Isnes (BE)

(72) Inventor: Noureddine Frid, Beersel (BE)

(73) Assignee: INTRESSA VASCULAR S.A., Gembloux (BE)

( * ) Notice: Subject to any disclaimer, the term of this patent is extended or adjusted under 35 U.S.C. 154(b) by 0 days.

(21) Appl. No.: 15/775,332

(22) PCT Filed: Nov. 10, 2016

(86) PCT No.: PCT/EP2016/077363
§ 371 (c)(1),
(2) Date: May 10, 2018

(87) PCT Pub. No.: WO2017/081213
PCT Pub. Date: May 18, 2017

(65) Prior Publication Data
US 2018/0325708 A1 Nov. 15, 2018

(30) Foreign Application Priority Data
Nov. 13, 2015 (IN) .......................... 3716/DEL/2015

(51) Int. Cl.
*A61F 2/01* (2006.01)
*A61F 2/90* (2013.01)
*A61F 2/06* (2013.01)
*A61F 2/82* (2013.01)

(52) U.S. Cl.
CPC .......... *A61F 2/90* (2013.01); *A61F 2002/068* (2013.01); *A61F 2002/823* (2013.01); *A61F 2210/0014* (2013.01); *A61F 2210/0076* (2013.01); *A61F 2230/0069* (2013.01)

(58) Field of Classification Search
CPC ........ A61F 2/86; A61F 2/90; A61F 2002/068; A61F 2002/823
See application file for complete search history.

(56) References Cited

U.S. PATENT DOCUMENTS

| 10,335,259 | B2 * | 7/2019 | Frid | ...................... A61L 31/022 |
| 2013/0245745 | A1 * | 9/2013 | Vong | ...................... A61F 2/885 623/1.12 |

* cited by examiner

*Primary Examiner* — Dinah Baria
(74) *Attorney, Agent, or Firm* — Gerald T. Gray; Leydig, Voit & Mayer, Ltd

(57) ABSTRACT

An implantable endoluminal prosthesis for use in the treatment of aneurysm involving branches is described, where at least one self-expandable braided framework extending along an axis is able to expand from a radially compressed state in a delivery configuration to a radially expanded state. The self-expandable braided framework includes a plurality of layers of wires made of biocompatible material forming a lattice with a plurality of wires of said layers; the wires being integrated in the mesh of at least one of the adjacent layers; the self-expandable braided framework including a lumen in a cylindrical form; characterized in that, in radially expanded state, a ratio of a thickness of a wall of the implantable endoluminal prosthesis in the radially expanded state to the diameter of wire being greater than 3.0; and the surface coverage ratio (SCR) of the braided framework is at least 30% and at most 50%.

13 Claims, 5 Drawing Sheets

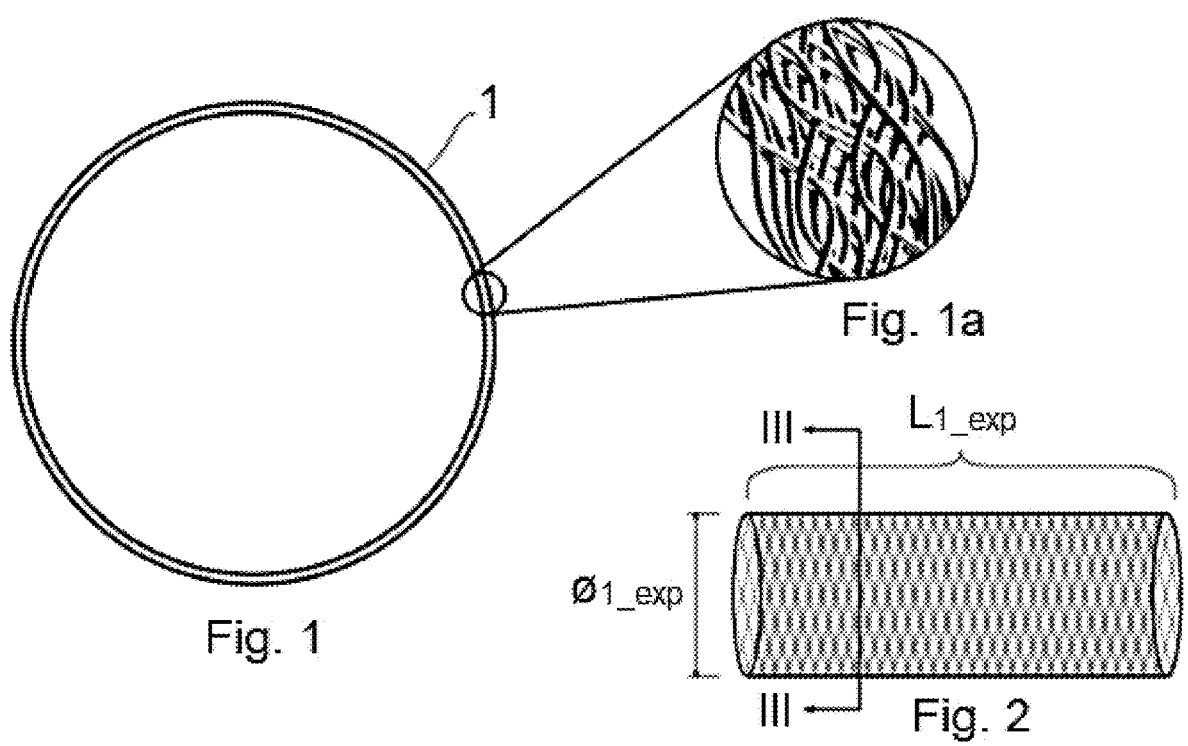
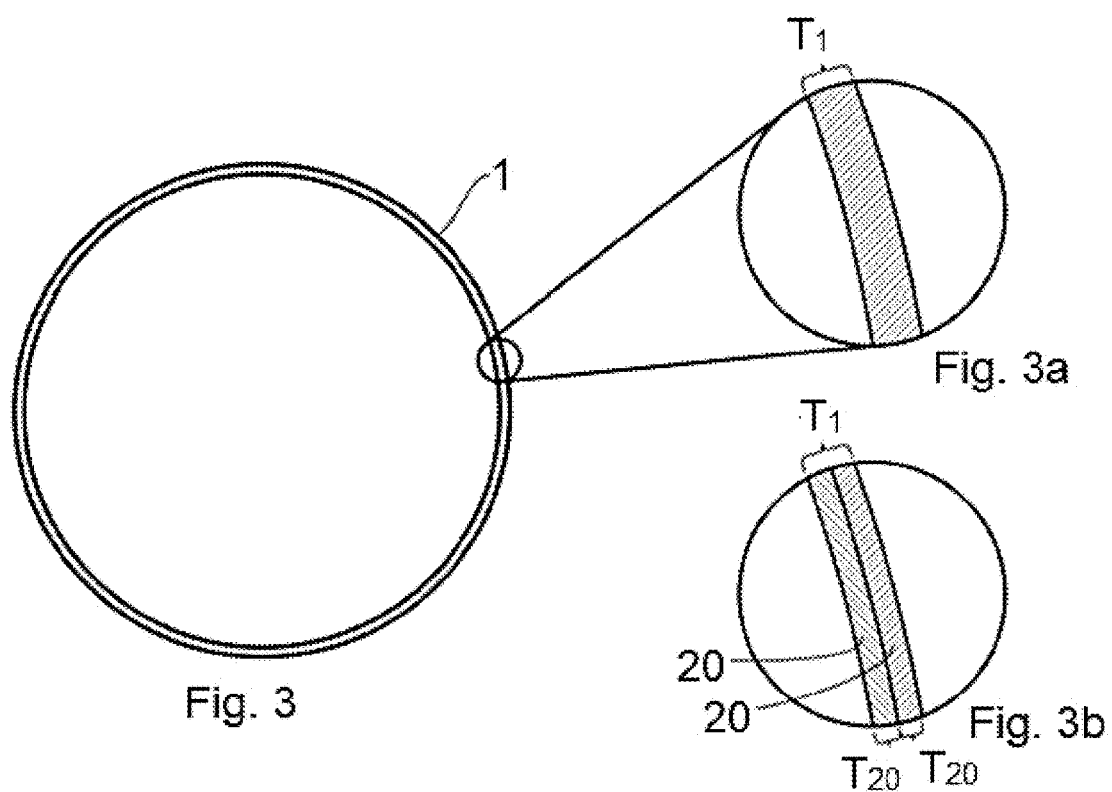

IMPLANTABLE ENDOLUMINAL PROSTHESIS

FIELD OF THE INVENTION

The present invention relates to implantable endoluminal prostheses. More particularly, it relates to an endoluminal prosthesis for treatment of aneurysm involving branches.

BACKGROUND OF THE INVENTION

Endovascular repair is known as a relatively new and minimally invasive technique for treatment of aortic aneurysm. It delivers an impermeable tube (graft) supported with metallic or plastic frame (stent) via a remote vessel. However, because of its impermeability, this technique cannot be applied to aneurysm repair in which the aneurysm involves important branches (e.g. the coronary arteries, the supra aortic branches, renal and middle suprarenal arteries, visceral arteries and internal iliac), otherwise it causes serious complications with occlusion of the branches.

SUMMARY OF THE INVENTION

A first object of the present invention is to provide a device implantable by endovascular approach for treatment of aneurysm involving branches.

Another object of the invention is ensuring patency of the branches while treating an aneurysm.

The subject of the present invention is defined in the appended independent claims. Preferred embodiment are defined in the depended claims.

A subject of the present invention is an implantable endoluminal prosthesis having a multilayer configuration and comprising at least one self-expandable braided framework. Said braided framework extends along an axis being able to expand from a radially compressed state in a delivery configuration to a radially expanded state. The braided framework is formed with at most 196 wires having a given diameter $\varnothing_{21}$. The braid framework is devoid of any impermeable cover layer and forms a wall of the endoluminal prosthesis. The braided framework comprises a lumen in a cylindrical form with a circular cross-section and a constant diameter. A ratio $T_1/\varnothing_{21}$ of thickness $T_1$ of a wall of said endoluminal prosthesis in radially expanded state to the diameter $\varnothing_{21}$ of wire being greater than 2.0, preferably at least 2.5, more preferably at least 3.0, even more preferably at least 3.5, still even more preferably 4.0. The surface coverage ratio (SCR) of said endoluminal prosthesis is more than 30% and less than 70%, preferably more than 35% and less than 50% in radially expanded state.

The self-expandable braided framework preferably comprises at least 90 wires and at most 130 wires; and the diameter of the wires is at least 120 μm, preferably at least 200 μm and at most 220 μm.

In another preferred embodiment, in radially expanded state, the self-expandable framework comprises a plurality of layers of wires made of biocompatible material; each layer forming a mesh; the meshes forming a lattice with a plurality of wires of said layers; the meshes being interlocked, the wires being integrated in the mesh of at least one of the adjacent layers.

BRIEF DESCRIPTION OF THE FIGURES

Other particularities and advantages of the invention will be developed hereinafter, reference being made to the appended drawings wherein:

FIG. 1 is a schematic front view of an endoluminal prosthesis according to the present invention FIG. 1a is a schematic magnified view of a portion of the front view shown in FIG. 1.

FIG. 2 is a side view of the endoluminal prosthesis shown in FIG. 1.

FIG. 3 is a section view of the endoluminal prosthesis shown in FIGS. 1, 1a and 2 according to a cutting plane III-III.

FIG. 3a is a schematic magnified view of an embodiment of a portion of the cross-section shown in FIG. 3.

FIG. 3b is a schematic magnified view of another embodiment of a portion of the cross-section shown in FIG. 3.

DETAILED DESCRIPTION OF THE INVENTION

Figure 4:
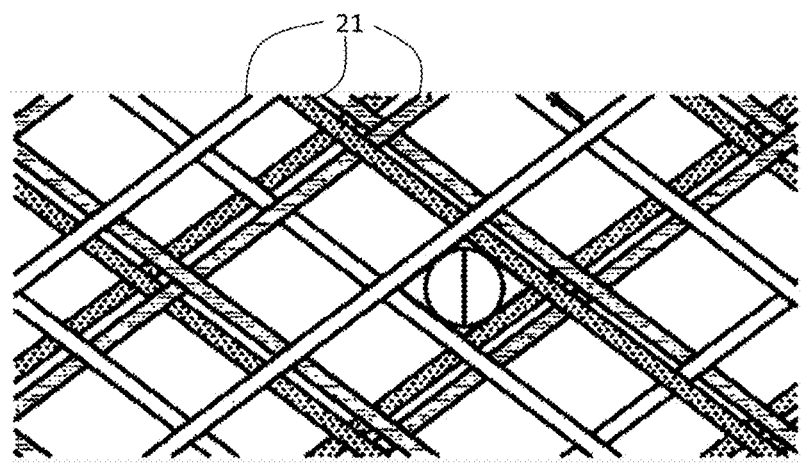
FIG. 4 is a schematic magnified view of another portion of an endoluminal prosthesis according to the present invention.

As used hereinafter, the term "implantable" refers to an ability of a medical device to be positioned at a location within a body vessel. Implantable medical device can be configured for transient placement within a body vessel during a medical intervention (e.g., seconds, minutes, hours), or to remain in a body vessel permanently.

The terms "endoluminal" or "transluminal" prosthesis refers to a device adapted for placement in a curved or straight body vessel by procedures wherein the prosthesis is advanced within and through the lumen of a body vessel from a remote location to a target site within the body vessel. In vascular procedures, a medical device can typically be introduced "endovascularly" using a catheter over a wire guide under fluoroscopic guidance. The catheters and wire guides may be introduced through conventional access sites in the vascular system.

The term "catheter" refers to a tube that is inserted into a blood vessel to access the target site. In the present description, a "catheter" will designate either a catheter per se, or a catheter with its accessories, meaning needle, guide wire, introducer sheath and other common suitable medical devices known by the man skilled in the art.

The term "permanent" refers to a medical device which may be placed in a blood vessel and will remain in the blood vessel for a long period of time (e.g. months, years) and possibly for the remainder of the patient's life.

The endoluminal prosthesis 1 is configured to take a compressed shape having a relatively small and relatively uniform diameter when disposed within a delivery system (i.e., "in compressed state"), and to spontaneously take a deployed shape with radially expanded diameter within the delivery location such as a body lumen (i.e., "in deployed state"). As used herein the terms "expanded shape" or "expanded state" refer to a shape or state resulting from the self-expanding properties of a self-spring-back object (e.g., braided framework 20) when it is allowed to expand without any outer compression force (i.e., non-constricted state). Beside these definitions, the term "nominal diameter" designates the diameter of the implantable endoluminal prosthesis when placed in the targeted vessel. Generally, the nominal diameter ($Ø_{nor}$) of a self-expandable device designed to be placed permanently inside a body lumen is 10 to 25% smaller than the external diameter of said device when deployed without external compression force ($Ø_{exp}$).

The implantable endoluminal prosthesis 1 according to the present invention comprises at least one self-expandable braided framework 20 able to expand from a radially compressed state in a delivery configuration to a radially expanded state. The implantable endoluminal prosthesis 1 has a multilayer configuration either comprising at least two of the self-expandable braided frameworks 20 or comprising at least one self-expandable braided framework 20 having a plurality of interlocked layers (interlocked multilayer configuration) formed by braiding a plurality of wires. The braided framework 20 comprises a lumen in a cylindrical form with a circular cross-section and a constant diameter shown in FIGS. 1, 1a and 2.

When the endoluminal prosthesis 1 having the multilayer configuration is observed normal with respect to a wall, meshes of the braided framework(s) 20 form a lattices with a plurality of level of wires 21. FIG. 3 shows a schematic cross-section of the endoluminal prosthesis 1 according to the present invention. FIG. 3a shows a schematic magnified view of a portion of the endoluminal prosthesis 1 comprising a self-expandable framework 20, and FIG. 3b showing a portion of the endoluminal prosthesis 1 comprising two self-expandable frameworks 20. A ratio $T_1/Ø_{21}$ of the thickness $T_1$ of a wall of the endoluminal prosthesis 1 to the diameter $Ø_{21}$ of wire 21 should be greater than 2.0. It characterizes the endoluminal prosthesis 1 having more than a single layer of mesh, namely multilayer configuration. The braided framework 20 is preferably made of a multilayer braid having a thickness $T_{20}$. The term "interlocked multilayer" refers to a framework comprising multiple layers, whose plies are not distinct at the time of braiding, for example a given number of wires of the plies of the first layer 20 being interlocked with the plies of the second layer 20 and/or other layers, for example, as schematically illustrated in FIG.4. Said interlocked multi-layer, for example, can be formed by using the braiding machine described in EP1248372.

Thanks to the thicker wall $T_1$ of the multilayered endoluminal prosthesis 1 as compared with the wall thickness of a conventional stent, endoluminal prosthesis 1 exhibits a three dimensional (3D) porosity. The thicker the wall is (regarding a given wire diameter $Ø_{21}$) the greater the 3D porosity effect.

Figure 5:
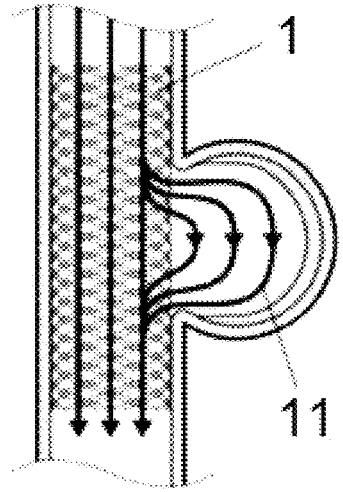
FIGS. 5 and 6 represent two stages of the healing process of an aneurysm wherein an endoluminal prosthesis according to the present invention has been implanted.

One of the technical effects provided by the 3D porosity of endoluminal prosthesis 1, is that the present endoluminal prosthesis 1 lets the blood flow into the aneurysm sac converts owing to its multilayer configuration, an undesired damaging turbulence in the aneurysmal sac into a smooth laminar flow 11 (as shown FIG. 5), instead of mechanically/physically keeping out the blood flow from the aneurysm as would do a conventional stent-graft techniques. It results in excluding the aneurysm by forming a protecting organized thrombus 12, known as layers of Zhan (see FIG. 6), while keeping the branches and collaterals unobstructed. Thanks to the permeable multilayer structure of the endoluminal prosthesis 1, additional repairs such as open debranching-bypass procedure and custom-made fenestrated/branched configuration for maintaining a blood flow are not required.

The surface coverage ratio (SCR) of endoluminal prosthesis 1 is between 30% and 70%, preferably more than 35% and less than 50%, even more preferably less than 45% in radially expanded state. The SCR of the endoluminal prosthesis is defined by the relation:

$$SCR=S_w/S_t$$

Wherein "$S_w$" is the actual surface covered by wires 21 composed in the endoluminal prosthesis 1, and "$S_t$" is the total surface are of the wall of the endoluminal prosthesis 1 when observed normal with respect to the wall.

Figure 7:
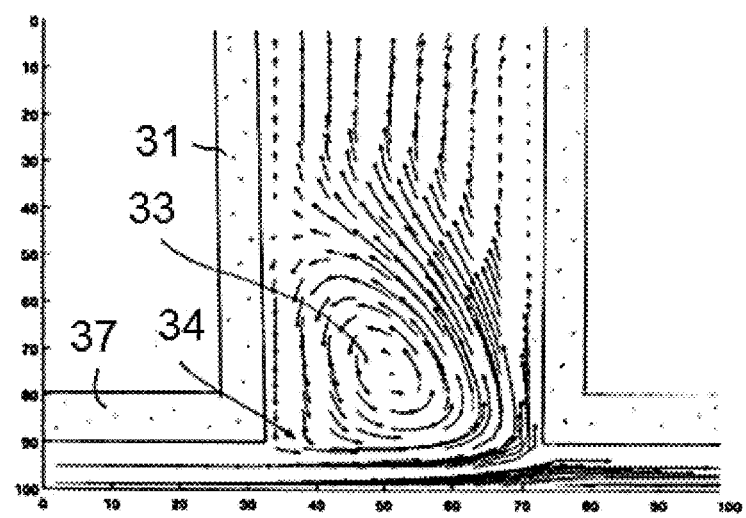
FIGS. 7 and 8 show simulations of blood velocity at an orifice of an aortic branch respectively according to prior art stents and with an endoluminal prosthesis according to the present invention.
Figure 8:
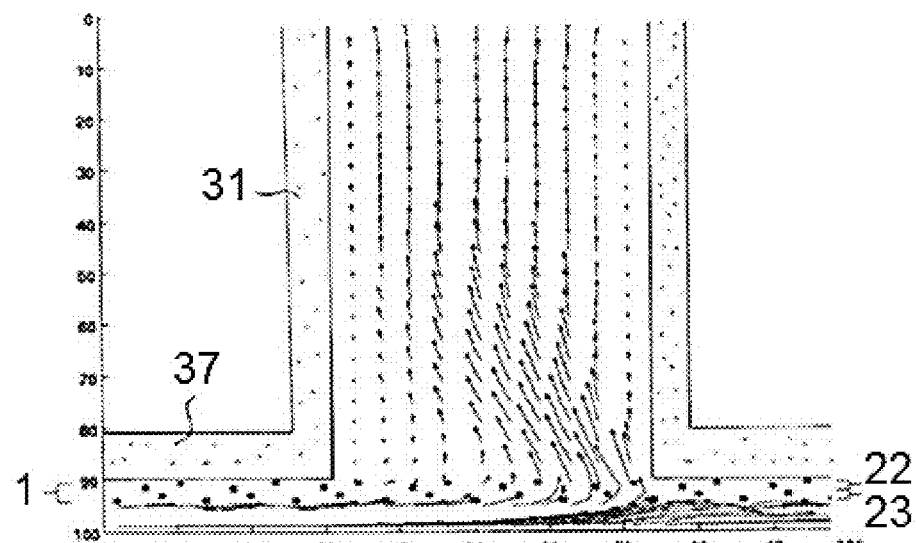
Figure 9A:
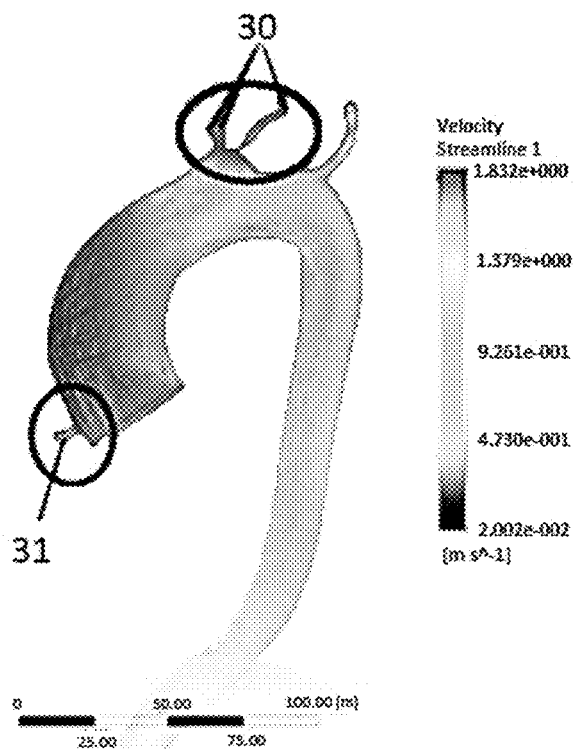
FIGS. 9a and 9b show simulation of blood velocity in an aortic model respectively according to the prior art (without stent) and with an endoluminal prosthesis according to the present invention.
Figure 9B:
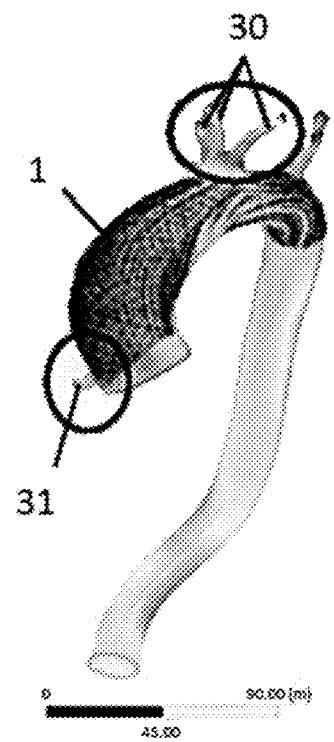
Figures 10A, 10B:
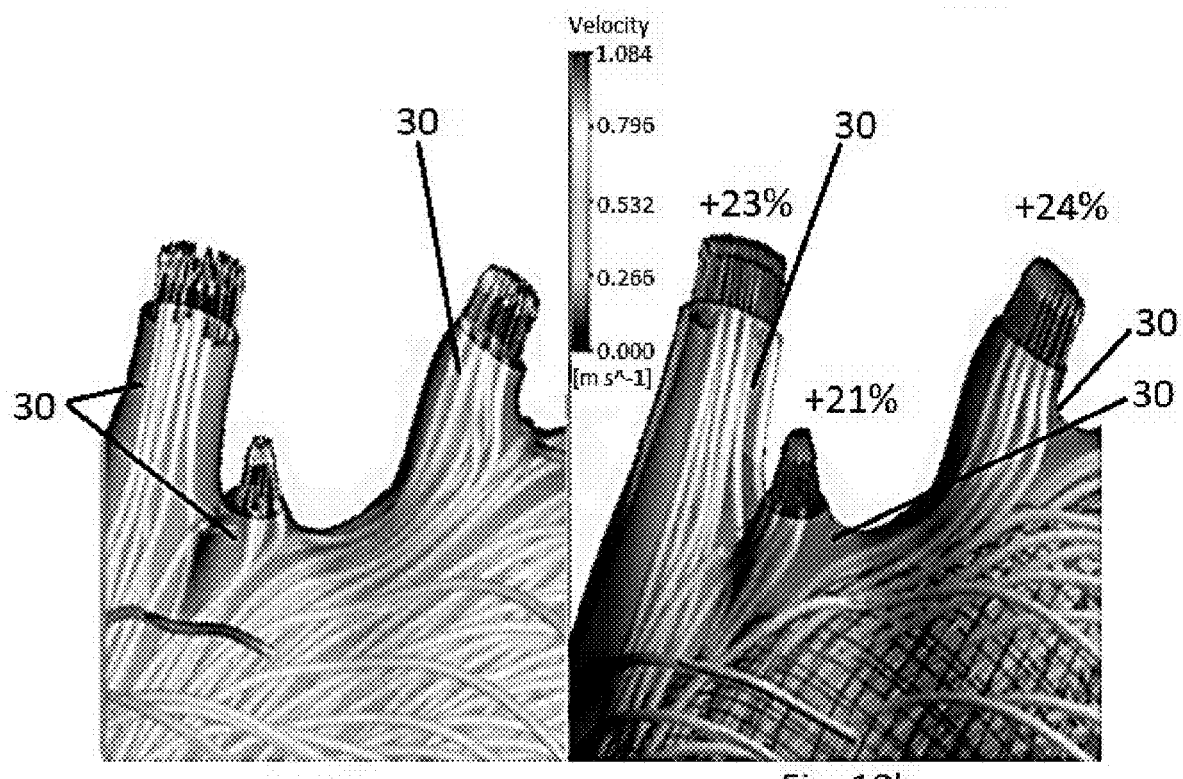
FIGS. 10a and 10b are magnified views at the supra aortic branches orifices of the simulations shown in FIGS. 9a and 9b, respectively.
Figures 11A, 11B:
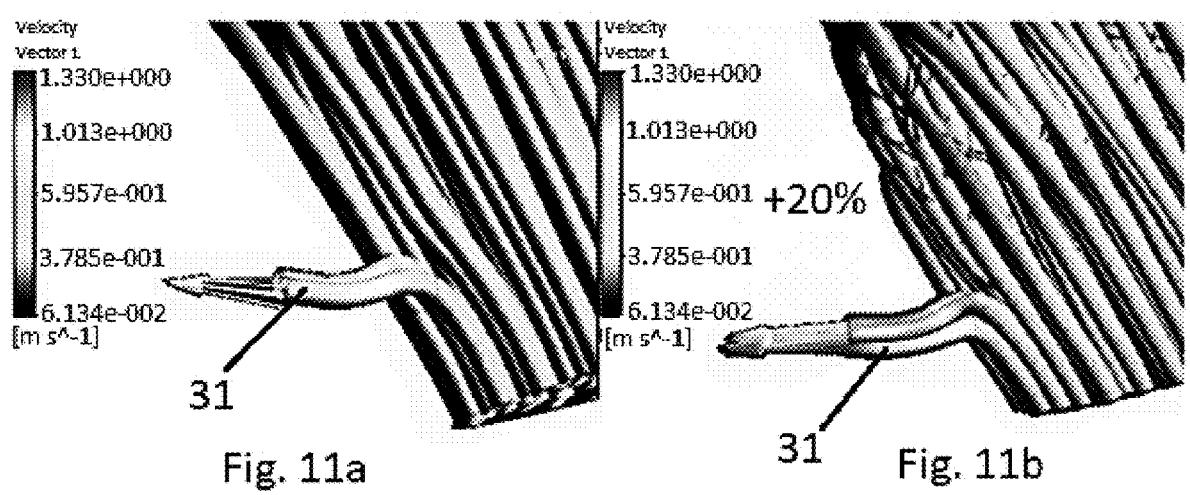
FIGS. 11a and 11b are magnified views at the coronaries orifice of the simulation shown in FIGS. 9a and 9b, respectively.

Studies and experiments carried by the inventor led to surprising and unexpected conclusions. The perfusion in branches is improved in accordance with the increase of the ratio $T_1/Ø_{21}$ having the SCR of the endoluminal prosthesis between 30% and 70% instead of occluding these blanches. "Perfusion" is, in physiology, the process of a body delivering blood to capillary bed in its biological tissue. The terms "hypoperfusion" and "hyperperfusion" measure the perfusion level relative to a tissue's current need to meet its metabolic needs. For example, the endoluminal prosthesis of the invention increases the perfusion in the supra aortic branches 30 when it covers the branches, resulting in that the functioning of the organs to which the supra aortic branches 30 carries the blood is improved. As shown in a simulation of FIG. 7, a heavy turbulence is created at an orifice 34 of branch. On the contray, when the endoluminal prosthesis is placed in front of the orifice 34, the chaotic flow is eliminated by passing through a wall of the endoluminal prosthesis and converted to a regulated laminar flow. It accelerates the flow in the branches covered by the endoluminal prosthesis 1. Accordingly, the ratio $T_1/Ø_{21}$ of the present endoluminal prosthesis 1 should be more than 2.0, preferably at least 2.5, more preferably at least 3.0, even more preferably at least 3.5, still even more preferably 4.0 while the SCR is between 30% and 70%, preferably between 35% and 50% in radially expanded state. A competed simulation of blood flow in an aorta model without and with the endoluminal prosthesis having more than 2.0 of $T_1/Ø_{21}$ are shown in FIGS. 9a and 9b, respectively. The aortic model was created based on an actual pathology of a patient. In FIG. 9b, the endoluminal prosthesis is placed so as to cover the wall of the vessel from the coronaries 31 up to the supra aortic branches 30. Processing so, surprisingly, the velocities of blood flow entering into the supra aortic branches 30 are notably increased of between 21% and 24% as shown in FIG. 10b (magnified view of FIG. 9b) at the orifices 34 of supra aortic branches 30, when compared with the velocity without device shown in FIG. 10a (magnified view of FIG. 9a). The flow velocity in the coronaries are also increased up to 20% as shown in FIGS. 11a and 11b.

Further distinguishing improvement of "perfusion" in the branches covered by the endoluminal prosthesis 1 was observed with this interlocked multilayer configuration. The braided framework 20 of the endoluminal prosthesis 1 is made of at most 196 wires 21, preferably at least 90 wires at most 130 wires. The wires preferably have a diameter ($Ø_{21}$) of at least 120 μm, preferably at least 150 μm, more preferably at least 180 μm, even more at least 200 μm and at most 220 μm.

Another advantages of the present invention is that the implantable endoluminal prosthesis 1, having higher value of the ratio $T_1/Ø_{21}$, can effectively form a thrombus in the aneurysmal sac in comparison with a braided framework having lower $T_1/Ø_{21}$ ratio. The ratio $T_1/Ø_{21}$ of the wall thickness $T_1$ of the endoluminal prosthesis 1 to the wire diameter $Ø_{21}$ of wire 21 being more than 2.0 characterizes the endoluminal prosthesis 1 having more than a single layer of mesh. The greater the ratio $T_1/Ø_{21}$, the more layers the endoluminal prosthesis 1 will comprise. Each wire forming multiple-layers works to make the blood flow be laminated which gets through the wall of the endoluminal prosthesis 1.

Figure 12:
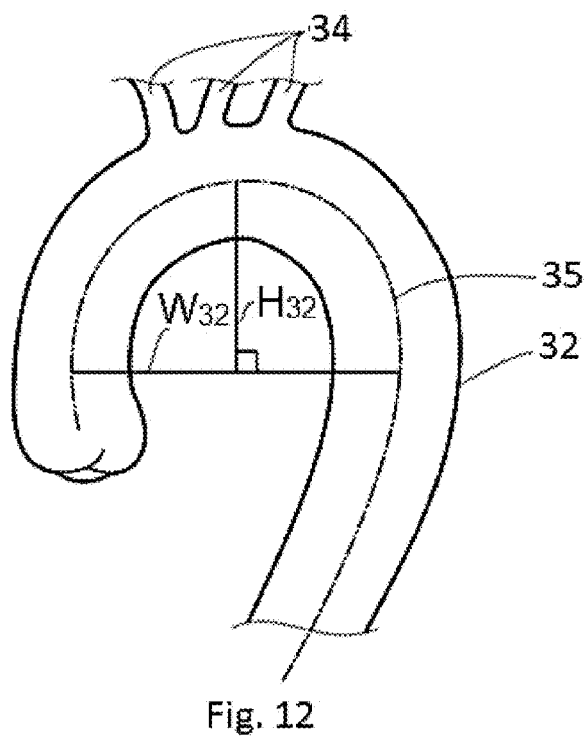
FIG. 12 is a schematic cross-section view of the aorta showing how to measure the width and height of the aortic arch.

The curve of the aortic arch 32 is generally defined by measuring the width $W_{32}$ and height $H_{32}$ of the curve as described by Ou et al. in *J. Thrac. Cardiovasc. Surg.* 2006; 132:1105-1111. Width $W_{32}$ is measured as the maximal horizontal distance between the midpoints 35 of the ascending and descending aorta 32 close to the axial plane going through the right pulmonary artery; and height $H_{32}$ of the aortic arch is measured maximal vertical distance between $W_{32}$ and the highest midpoint 35 of the aortic arch $W_{32}$ as depicted in FIG. 12.

Interlocked multiple-layer configuration having a ratio $T_1/Ø_{21}$ of at least 2.5 brings an important advantageous technical property. When the aneurysm is located at the outer side of the curve, it is most important to set an optimal SCR and an optimal opening size of mesh at the outer side of the curve in order to form a protecting organized thrombus in the aneurysmal sac by converting an undesired damaging turbulence 33 into a smooth laminar flow 36 while keeping branches, such as supra aortic branches 30, patent. Wires of the interlocked multiple-layer configuration of the invention shift to keep a regular distance between adjacent parallel, resulting in that the SCR can stays almost the same between in a curved state and in straight configuration. On the Contrary, when a conventional single-layer mesh-like tube having less than 2.0 of $T_1/Ø_{21}$ is deployed in a curved lumen, the SCR at the outer side of the curve are much lower than the SCR in a straight configuration. Therefore, the ratio $T_1/Ø_{21}$ of the present endoluminal prosthesis 1 should be more than 2.0, preferably at least 2.5, more preferably at least 3.0, even more preferably at least 3.5, still even more preferably at least 4.0.

Figure 6:
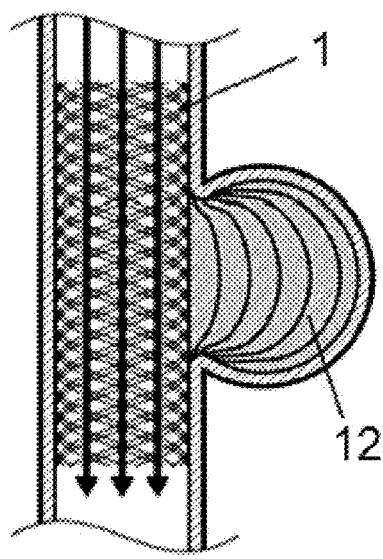
Figure 13:
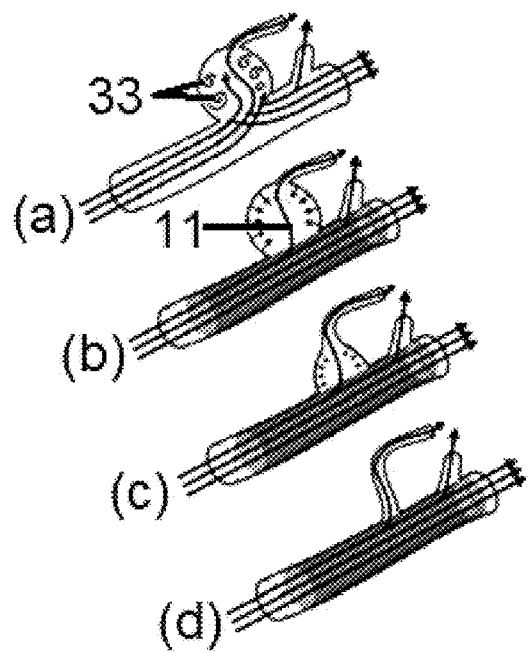
FIG. 13 (a-d) show the different phases of the healing process of a saccular aneurysm involving a branch with an endoluminal prosthesis according to the present invention.
Figure 14:
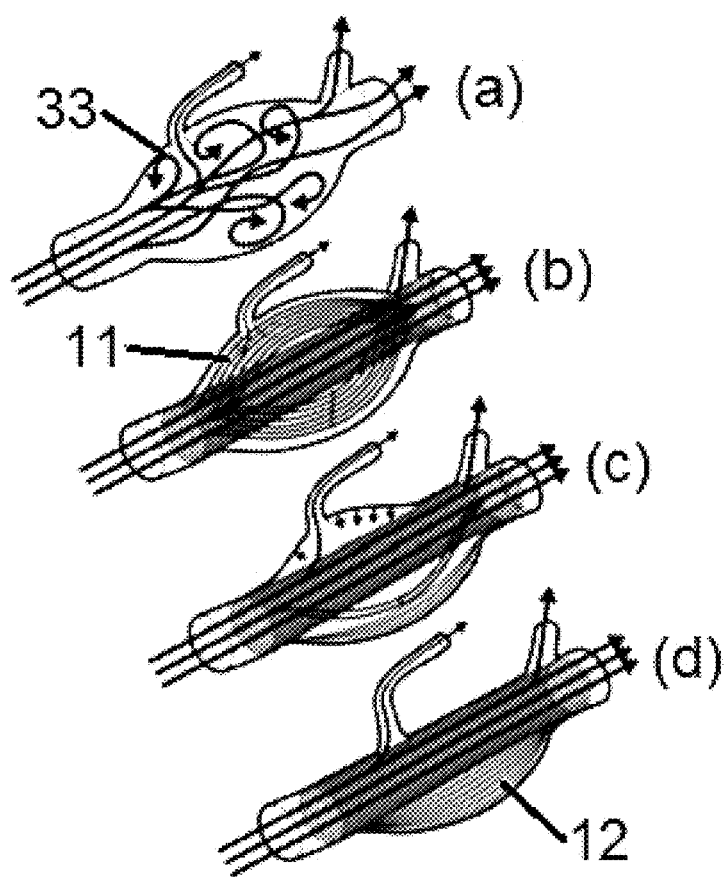
FIG. 14 (a-d) shows the different phases of the healing process of a fusiform-shaped aneurysm involving a branch with an endoluminal prosthesis according to the present invention.

As another surprising effect provided the present endoluminal prosthesis 1 having interlocked multiple-layer configuration, against the "normal" expectation that a space between an aneurysmal wall and endoluminal prosthesis would be occluded by thrombus as shown in FIG. 6, the aneurysm including branches shrinks directly instead of forming thrombus in the aneurysmal sac while still maintaining the blood flow into the branches as shown FIGS. 13 and 14. The inventor assumes that by sealing the beginning of the aorta with the enlarged, undesired turbulence 33 are eliminated and desired smooth flow 11 are created in this volume. It accelerates the non-turbulent blood flow entering the branches while decreasing the pressure under Venturi effect, resulting in shrinkage of the aneurysmal sac.

The biocompatible material used in the invention is preferably a metallic substrate selected from a group consisting of stainless steels (e.g., 316, 316L or 304); nickel-titanium alloys including shape memory or superelastic types (e.g., nitinol, Nitinol-DFT®-Platinum); cobalt-chrome alloys (e.g., elgiloy); cobalt-chromium-nickel alloys (e.g., phynox); alloys of cobalt, nickel, chromium and molybdenum (e.g., MP35N or MP20N); cobalt-chromium-vanadium alloys; cobalt-chromium-tungsten alloys; magnesium alloys; titanium alloys (e.g., TiC, TiN); tantalum alloys (e.g., TaC, TaN); L605. Said metallic substrate is preferably selected from the group consisting of titanium, nickel-titanium alloys such as nitinol and Nitinol-DFT®-Platinum, any type of stainless steels, or a cobalt-chromium-nickel alloys such as Phynox®.

The invention claimed is:

1. An implantable endoluminal prosthesis having an interlocked multilayer configuration, the implantable endoluminal prosthesis consisting essentially of:
    a self-expandable braided framework including a plurality of layers of wires made of a biocompatible material, the self-expandable braided framework extending along an axis and able to expand from a radially compressed state in a delivery configuration to a radially expanded state;
    wherein:
        each layer in the plurality of layers includes a plurality of wires having a given diameter and forming a mesh, wherein plies of the mesh are not distinct at the time of braiding, and a given number of wires of the plies of the first layer being interlocked with the plies of the second layer and/or other layers;
        a surface coverage ratio (SCR) of the self-expandable braided framework in the radially expanded state is at least 30% and at most 40%;
        a ratio ($T_1/Ø_{21}$) of a thickness of a wall of the implantable endoluminal prosthesis, in the radially expanded state, to a diameter of the wire is at least 3.0; and
        wires of the interlocked multiple-layer configuration shift to keep a regular distance between adjacent parallel wires, resulting in that the SCR is maintained between a curved state and a straight configuration, each wire in the plurality of wires having a diameter ($Ø_{21}$) of at least 150 μm.

2. The implantable endoluminal prosthesis according to claim 1, wherein the ratio ($T_1/Ø_{21}$) is at least 4.0.

3. The implantable endoluminal prosthesis according to claim 1, wherein the self-expandable braided framework includes at least 90 wires and at most 130 wires.

4. The implantable endoluminal prosthesis according to claim 1 wherein the wire diameter ($Ø_{21}$) of each wire in the plurality of wires is at least 180 μm.

5. The implantable endoluminal prosthesis according to claim 1 wherein the wire diameter ($Ø_{21}$) of each wire in the plurality of wires is at least 200 μm and at most 220 μm.

6. The implantable endoluminal prosthesis according to claim 1, wherein the biocompatible material is a metallic substrate selected from the group consisting of: titanium, a nickel-titanium alloy, a stainless steel, and a cobalt-chromium-nickel alloy.

7. The implantable endoluminal prosthesis according to claim 1, wherein each wire in the plurality of wires has a diameter ($Ø_{21}$) of more than 150 μm.

8. An implantable endoluminal prosthesis consisting essentially of:
    a plurality of wires having a given diameter and forming a self-expandable braided framework capable of being implanted into a lumen of a body vessel, wherein the self-expandable braided framework is delivered into the lumen in a radially compressed state and expands to a radially expanded state, wherein:
- the self-expandable braided framework includes multiple interlocked layers forming, in the radially expanded state, a porous wall, wherein plies of the multiple interlocked layers are not distinct at the time of braiding, and a given number of wires of the plies of the first layer being interlocked with the plies of the second layer and/or other layers;
- the self-expandable braided framework, in the radially expanded state, has a surface coverage ratio (SCR) between 30% and 40%;
- a diameter ($\varnothing_{21}$) of each wire in the plurality of wires is at least 150 µm;
- a ratio ($T_1/\varnothing_{21}$) of a thickness of a wall of the implantable endoluminal prosthesis, in the radially expanded state, to a diameter of the wire is at least 3.0; and
- the wires of the interlocked multiple-layer configuration shift to keep a regular distance between adjacent parallel wires, resulting in that the SCR is maintained between a curved state and a straight configuration.

9. The implantable endoluminal prosthesis of claim 8, wherein a thickness of the porous wall is at least four times the diameter of each wire in the plurality of wires.

10. The implantable endoluminal prosthesis of claim 8, wherein the diameter of each wire in the plurality of wires is at least 200 µm and at most 220 µm.

11. The implantable endoluminal prosthesis of claim 8, wherein a total number of wires in the self-expandable braided framework is at least 90 wires and less than 130 wires.

12. The implantable endoluminal prosthesis of claim 8, wherein the wires comprise a biocompatible metallic substrate selected from the group consisting of: stainless steel; nickel-titanium alloys; cobalt-chrome alloys; cobalt-chromium-nickel alloys; alloys of cobalt, nickel, chromium, and molybdenum; cobalt-chromium-vanadium alloys; cobalt-chromium-tungsten alloys; magnesium alloys; titanium alloys; and tantalum alloys.

13. The implantable endoluminal prosthesis according to claim 8, wherein the diameter ($\varnothing_{21}$) of each wire in the plurality of wires is more than 150 µm.

* * * * *